United States Patent
Kinkade, Jr.

(10) Patent No.: US 7,520,163 B2
(45) Date of Patent: Apr. 21, 2009

(54) SULFUR IN FUEL TESTER

(75) Inventor: Charles E. Kinkade, Jr., Warren, MI (US)

(73) Assignee: SPX Corporation, Charlotte, NC (US)

( * ) Notice: Subject to any disclaimer, the term of this patent is extended or adjusted under 35 U.S.C. 154(b) by 34 days.

(21) Appl. No.: 11/812,874

(22) Filed: Jun. 22, 2007

(65) Prior Publication Data

US 2008/0314127 A1 Dec. 25, 2008

(51) Int. Cl.
  *G01N 33/22* (2006.01)
  *G01N 25/02* (2006.01)

(52) U.S. Cl. .................. 73/61.41; 73/23.2; 436/123

(58) Field of Classification Search ............... 73/23.31, 73/61.46, 61.76, 61.77, 23.2, 61.41; 436/60, 436/119, 122, 123; 422/61
See application file for complete search history.

(56) References Cited

U.S. PATENT DOCUMENTS

| | | | | |
|---|---|---|---|---|
| 3,025,698 A | * | 3/1962 | Fuhrmann et al. | 73/60.11 |
| 3,838,969 A | * | 10/1974 | Dugan | 436/115 |
| 3,880,587 A | * | 4/1975 | Szakasits et al. | 436/123 |
| 4,120,659 A | * | 10/1978 | Cropper | 436/123 |
| 4,409,336 A | * | 10/1983 | Oita | 436/123 |
| 4,569,918 A | * | 2/1986 | Moore et al. | 436/122 |
| 4,617,278 A | * | 10/1986 | Reed | 436/60 |
| 5,049,508 A | * | 9/1991 | Hilscher et al. | 436/123 |
| 5,152,963 A | * | 10/1992 | Wreyford | 422/80 |
| 6,716,336 B2 | * | 4/2004 | Hurland et al. | 205/786.5 |
| 6,746,587 B2 | * | 6/2004 | Saffell et al. | 204/432 |
| 2004/0151630 A1 | * | 8/2004 | Hernandez et al. | 422/80 |

FOREIGN PATENT DOCUMENTS

| | | | |
|---|---|---|---|
| DE | 4231510 A1 | * | 11/1993 |
| DE | 10316810 A1 | * | 11/2004 |
| WO | WO 9219964 A1 | * | 11/1992 |

* cited by examiner

*Primary Examiner*—John Fitzgerald
(74) *Attorney, Agent, or Firm*—Baker & Hostetler LLP

(57) ABSTRACT

A portable diesel fuel tester and a method of its use are provided. A sample of diesel fuel is placed in a sample tray of the tester. The diesel fuel is heated to a gas state and circulated to a $SO_2$ sensor by an air pump. The $SO_2$ sensor determines the level of sulfur in the diesel fuel based on the $SO_2$ levels. The sulfur level is displayed on an LCD screen for viewing by the user.

20 Claims, 3 Drawing Sheets

SULFUR IN FUEL TESTER

FIELD OF THE INVENTION

The present invention relates generally to a fuel tester. More particularly, the present invention relates to a portable diesel fuel tester.

BACKGROUND OF THE INVENTION

Ultra-low sulfur diesel (ULSD) is a new standard that has been proposed by the EPA that effects diesel fuel sold for use on-road. This new regulation pertains to diesel fuel, additives and distillate fuels such as kerosene. The previous low diesel sulfur content was 500 p.p.m. (parts per million). The USLD contains only 15 p.p.m., which is about a 97 percent reduction from the 500 p.p.m. level.

The EPA requires that by Dec. 1, 2010, all highway diesel fuel sold will be ULSD. The use of ULSD will decrease emissions of sulfur compounds, which has been linked to acid rain. The decrease in sulfur content (15 p.p.m.) will reduce the replacement of particulate filters, which are being plugged up at the higher sulfur content of 500 p.p.m. The EPA hopes that the new standard will reduce the nitrogen oxide emissions by 2.6 million tons and particulate matter by 110,000 tons per year. Additionally, ULSD is required to be used in the new diesel engines or the warranty of the engines will be voided.

There are currently bench size testers that are implemented with a computer that are expensive to purchase and use. The bench size testers are not mobile and thus field inspections cannot be readily be done either at the refineries or the fueling stations. Additionally, the bench size testers require that the samples be sent to its location for analysis and that increases the time in which the results can be made available. The inspections include determining whether there has been sulfur contamination in the fuel refining system or if the fuel is over the legal limit. When sulfur reacts with oxygen it forms $SO_2$, which can be used to test the amount of sulfur in the fuel.

Accordingly, there is a need for an apparatus and method to test diesel fuel in the field that is cost effective and the results can be determined in the field.

SUMMARY OF THE INVENTION

The foregoing needs are met, to a great extent, by the present invention, wherein in one aspect an apparatus is provided that in some embodiments provides a vehicle diagnostic device that includes a programmable function key in order to control a function on an emission computer workstation.

In accordance with one embodiment of the present invention, a portable diesel fuel tester is provided, which can include a LCD display that displays testing information, a testing chamber for testing the diesel fuel having a door, the door having vent holes that can vent a gas from the testing chamber, a sample tray located in the testing chamber that can receive a sample of diesel fuel to be tested, the sample tray having a heating element that can heat the diesel fuel to the gas state, a $SO_2$ sensor that senses $SO_2$ gas generated by the heating of the diesel fuel, an air pump that can circulate the gas of the heated diesel fuel from the sample tray to the $SO_2$ sensor, a power source for powering the fuel tester, a processor having a software that can operate the tester, wherein the processor can be in communication with the LCD display, the $SO_2$ sensor, the heating element, the power source and the air pump, and a housing that can house the LCD display, the testing chamber, the sample tray, the $SO_2$ sensor, the processor, the power source, and the air pump, wherein the housing is configured so that the tester is portable.

In accordance with another embodiment of the present invention, a method of testing a sample of diesel fuel is provided and can include depositing a sample of diesel fuel on a sample tray of a portable diesel fuel tester, heating the sample of diesel fuel with a heating element to a gas state that is detectable by a $SO_2$ sensor, circulating the gas from the sample tray to the $SO_2$ sensor with an air pump, detecting the gas containing $SO_2$ with the $SO_2$ sensor, determining the amount of sulfur in the sample of diesel fuel from the $SO_2$ gas, and displaying the amount of sulfur in the sample of diesel fuel on a LCD display.

In accordance with yet another embodiment of the present invention, a portable diesel fuel tester is provided, which can include a means for displaying testing information, a means for containing testing conditions for a sample of diesel fuel having a door, the door having vent holes that can vent a gas from the means for containing testing conditions, a means for receiving the sample of diesel fuel to be tested, the means for receiving having a means for heating the diesel fuel to the gas state, a means for sensing $SO_2$ gas generated by the heating of the diesel fuel, a means for circulating the gas of the heated diesel fuel from the means for receiving to the means for sensing, a means for powering the portable diesel fuel tester, a means for processing having a software that operates the tester, wherein the means for processing is in communication with the means for displaying, the means for sensing, the means for heating, means for the powering and the means for circulating, and a means for housing that houses the means for displaying, the means for containing, the means for receiving, the means for sensing, the means for processing, the means for powering, and the means for circulating, wherein the means for housing is configured so that the tester is portable.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
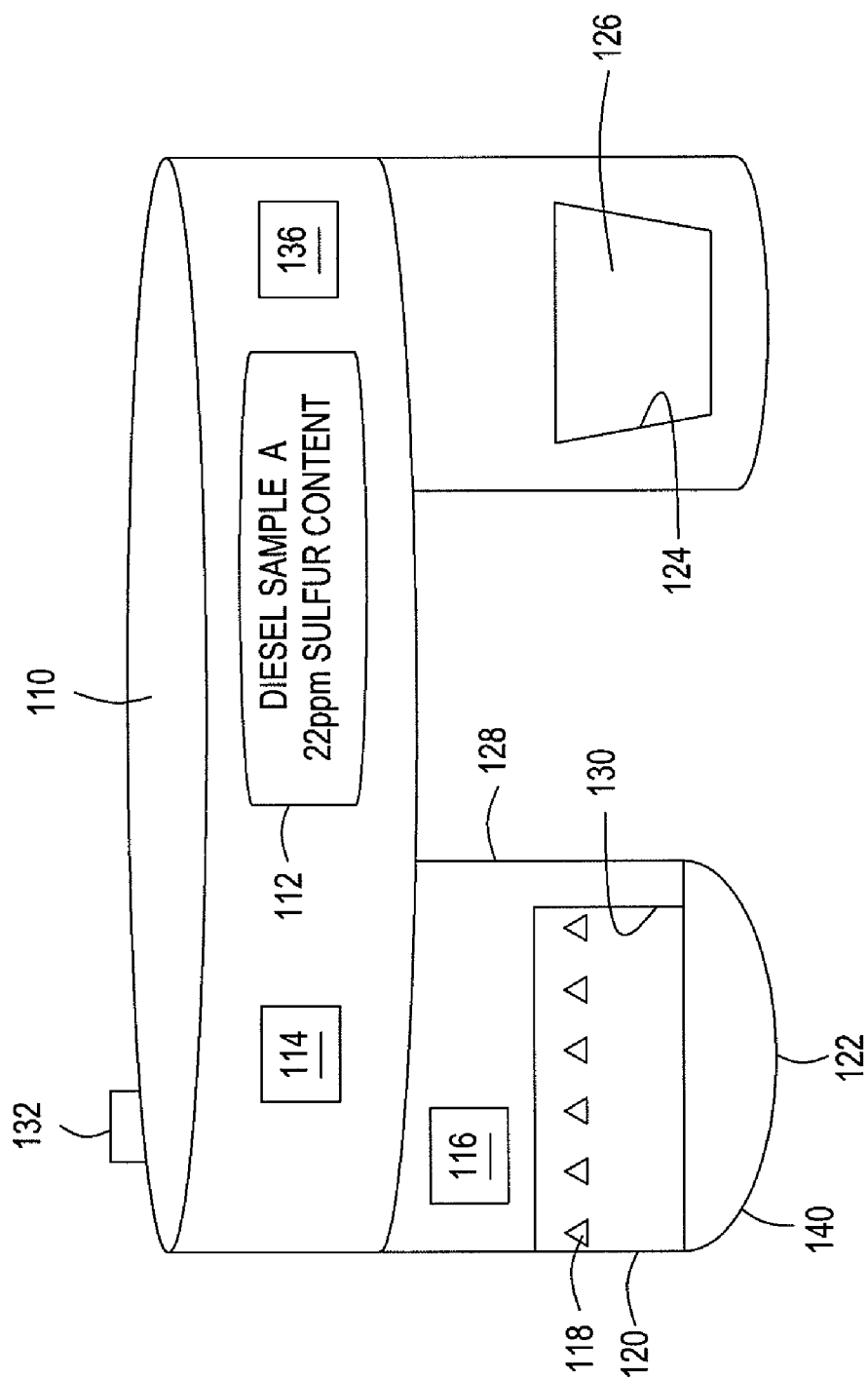
FIG. 1 illustrates a diesel fuel tester according to an embodiment of the invention.

The invention will now be described with reference to the drawing figures, in which like reference numerals refer to like parts throughout. An embodiment in accordance with the present invention provides a portable diesel fuel tester that can test the sulfur content in the field and display the results to a user.

FIG. 1 illustrates a diesel fuel tester 100 according to an embodiment of the invention. The tester is configured and designed to be portable. The tester 100 includes a housing 110 to house the components of the tester including a testing portion 128, a storage compartment 124, and power switch 132 and a power source 136, such as a battery (not shown). The tester further includes an LCD screen 112 mounted on an external surface of the housing for viewing by the user. The LCD displays information including the amount of sulfur in the tested diesel fuel. The LCD can also display instructions on the screen for the user to run the test or display any other information desired. The power source can be an internal or external battery or by plugging into a DC or AC source.

Within the housing 110 is a circulating air pump 114 to circulate the air in the testing portion 128 of the tester 100. A $SO_2$ sensor 116, such as sensors available from Alphasense, Ltd in the United Kingdom can be used to measure the amount of sulfur in the tested diesel fuel. A door 120, made from Plexiglas, for example, is used to introduce the diesel fuel into a testing chamber 130. The door 120 can include vent holes 118 therein for the vapor (from the vaporized diesel fuel) to escape the testing chamber 130 to reach the $SO_2$ sensor. A sample tray 122 that includes a resistive heating element 140 is located at the bottom of the testing chamber 130.

The testing portion 128 is used to test a sample of the diesel fuel. Only a small sample, such as 2-10 drops of the diesel fuel is needed. The sample can be collected from any sized liquid dropper. The $SO_2$ sensor can be any sensor that can measure the vapor or gas of the tested diesel fuel to determine if it is within the 15 p.p.m. required by the EPA. The sensitivity of the sensor can be from about 5 p.p.m. to about 50 p.p.m. or any other sensitivity level can be used by the user so long it is within the desired testing range.

The door 120 is used to contain the vapor gas until it escapes from the vent holes 118. The door 120 can include a handle (not shown) and hinges (not shown) for easy opening and closing. The door 120 can be made from any material including polymers, metals or alloys so long as they do not react with the $SO_2$ or the diesel fuel being tested. Although shown as triangular in shape, the vent holes 118 can be any shape including circular, rectangular, oval, elliptical, and a combination thereof. The size of the vent holes can be any size so long as they allow a detectable amount of vapor to reach the sensor. The holes can range, for example, from 1 mm to 50 mm. However, other larger or smaller sizes are also contemplated by the invention.

The sample tray 122 can be made from any material so long as it can be heated to a temperature that exceeds the flash point/boiling point of any diesel fuel that is tested. The heating time can range, for example, from about 2 seconds to about 45 seconds. The heating time can be lower or higher than the aforementioned times due to various types of diesel fuel that can be tested.

The diesel fuel needs to be vaporized so that it mixes with the 02 in the surrounding atmosphere to form $SO_2$ that the sensor can detect and quantify. The sample tray 122 includes a heating element such as a resistive heating element made from Nichrome. The heating element is used to heat the diesel fuel in the sample tray to the boiling point. The heating element can be integral or separated from the heating tray.

An air pump is used to circulate the air in the testing chamber 130 so that the $SO_2$ sample can reach the $SO_2$ sensor for an accurate reading. The air pump can be any capacity pump so long as it can adequately circulate the air within the testing portion of the tester.

Within the housing a storage compartment 124 is provided and contains a cleaning tray 126. The cleaning tray includes alcohol wipes and cleaning cloth. Other wipes and cleaning supplies are within the spirit of the invention. The wipes are used to clean the sample tray and the cleaning cloth is used to dry and remove any remaining residue on the sample tray. The wipes and the cleaning cloth should be the kinds that do not leave any residue, felt or otherwise contaminate the sample tray.

Figure 2:
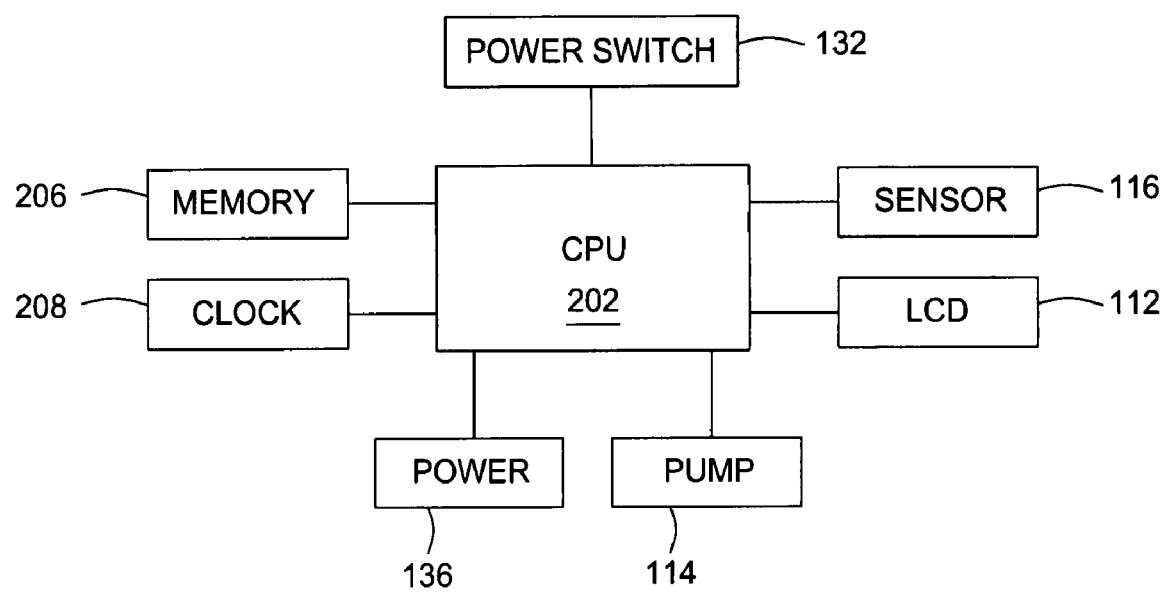
FIG. 2 is a block diagram of the components of the tester.

FIG. 2 is block diagram of the components of the tester 100. A processor 202 or CPU (central processing unit) is provided to operate the tester 100. In alternative embodiments, the processor can be an FPGA (Field Programmable Gate Array) or other controllers known in the art. The processor 202 communicates with the power switch 132, the power source 136, the sensor 116, the LCD 112, and the pump 114. The processor includes volatile memory (RAM) and non-volatile memory 206 to store programming that operates the tester 100. The CPU can have an external clock 208 or an internal clock. As stated above, the processor can allow communication between the components in order for the tests to be conducted by the tester and the results displayed on the LCD.

Figure 3:
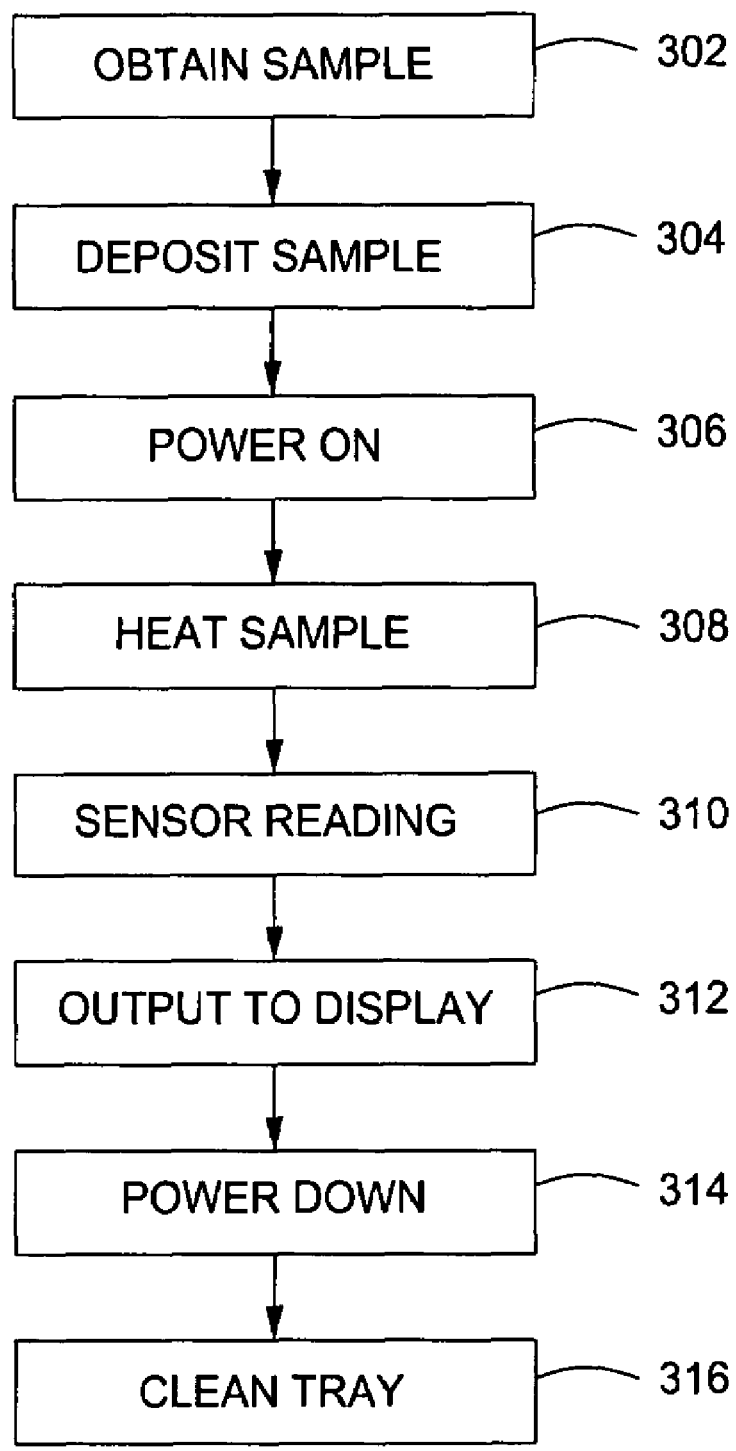
FIG. 3 illustrates the steps of the operation of the tester of the present invention.

FIG. 3 illustrates the steps of the operation of the tester of the present invention. At step 302, a sample of the diesel fuel to be tested is obtained. The sample can be obtained in a dropper known in art. At step 304, the door is opened and the sample is deposited on the sample tray. The sample can be a few drops in amount from the dropper. The door is closed so the test can be conducted. At step 306, the tester is turned on via the power switch 132, which activates the heating element and the air pump. The LCD can also display "Place Sample" and "Press Start" in order to instruct the user. At step 308, the sample is heated for about 30 seconds or so to its vaporized form. The heating time can be more or less than 30 seconds depending on the type of diesel fuel being tested. The LCD can display "Test In Progress," to let the user know that the test has begun. The pump helps to circulate the air and helps the vapor to exit the testing chamber through the vent holes in the door.

At step 310, the sensor takes a reading of the sample. As the vapor passes the sensor, the sensor senses the amount of $SO_2$ present. At step 312, the sensor outputs the reading to the LCD. The LCD can display on one line, the sample letter, for example, "Diesel Sample A," and on a second line, the sulfur content, for example, "23 p.p.m. sulfur content." If a reading can not determined accurately, high or low sulfur content can be shown on the display or on another indicator such as an LED (not shown, red for high sulfur and green for low sulfur). The high or low indicator can be based on a 30 p.p.m. cutoff range, wherein below 30 p.p.m., the tester will indicate low sulfur and above 30 p.p.m. the tester will indicate high sulfur. In the mean time, the pump still circulates the air for an additional 30 seconds or so after the diesel fuel vaporized to evacuate any remaining vapors from the testing chamber.

In other embodiments, additional steps include step 314, where the user power downs the tester 100 via the power switch 132. At step 316, the user can clean the testing chamber and the sample tray with the wipe and cloth stored in the cleaning tray. After cleaning, the tester is ready to run the next sample.

The tester 100 is designed to be portable so that it can be used in the field. A relatively small sample is needed and the results can be determined in the field.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A portable diesel fuel tester, comprising:
a LCD display that displays testing information;
a testing chamber for testing a diesel fuel having a door, the door having vent holes that vents a gas from the testing chamber;
a sample tray located in the testing chamber that receives a sample of diesel fuel to be tested, the sample tray having a heating element that heats the diesel fuel to a-gas state;
a $SO_2$ sensor that senses $SO_2$ gas generated by the heating of the diesel fuel;
an air pump that circulates the gas of the heated diesel fuel from the sample tray to the $SO_2$ sensor;
a power source for powering the fuel tester;
a processor having a software that operates the tester, wherein the processor is in communication with the LCD display, the $SO_2$ sensor, the heating element, the power source and the air pump; and
a housing that houses the LCD display, the testing chamber, the sample tray, the $SO_2$ sensor, the processor, the power source, and the air pump, wherein the housing is configured so that the tester is portable.

2. The tester of claim 1, further comprising a storage compartment that stores a cleaning tray.

3. The tester of claim 1, wherein the $SO_2$ sensor and the sample tray are located within the testing chamber.

4. The tester of claim 1, wherein the heating element heats the diesel fuel to the gas form so that the $SO_2$ sensor can sense the $SO_2$ content in the gas and determine a sulfur amount in the diesel fuel.

5. The tester of claim 1, wherein the $SO_2$ sensor can detect the $SO_2$ levels from about 5 p.p.m. to about 50 p.p.m.

6. The tester of claim 1 further comprising of LEDs to indicate that the sulfur level is high or low in relation to a predetermined sulfur level.

7. The tester of claim 1, wherein the information can be directions to test the sample of diesel fuel and the amount of sulfur in the sample.

8. A method of testing a sample of diesel fuel, comprising:
depositing a sample of diesel fuel on a sample tray of a portable diesel fuel tester;
heating the sample of diesel fuel with a heating element to a gas state that is detectable by a $SO_2$ sensor;
circulating the gas from the sample tray to the $SO_2$ sensor with an air pump;
detecting the gas containing $SO_2$ with the $SO_2$ sensor;
determining the amount of sulfur in the sample of diesel fuel from the $SO_2$ gas; and
displaying the amount of sulfur in the sample of diesel fuel on a LCD display.

9. The method of claim 8 further comprising cleaning the sample tray before depositing the next sample.

10. The method of claim 8 further comprising displaying instructions on how to conduct the test of the sample of diesel fuel on the LCD display.

11. The method of claim 9 further comprising indicating on LEDs when the sulfur content in the sample of diesel fuel is higher or lower than a predetermined sulfur level.

12. The method of claim 9, wherein heating the sample with the heating element for about 2 seconds to about 45 seconds.

13. A portable diesel fuel tester, comprising:
a means for displaying testing information;
a means for containing testing conditions for a sample of diesel fuel having a door, the door having vent holes that vents a gas from the means for containing testing conditions;
a means for receiving the sample of diesel fuel to be tested, the means for receiving having a means for heating the diesel fuel to the gas state;
a means for sensing $SO_2$ gas generated by the heating of the diesel fuel;
a means for circulating the gas of the heated diesel fuel from the means for receiving to the means for sensing;
a means for powering the portable diesel fuel tester;
a means for processing having a software that operates the tester, wherein the means for processing is in communication with the means for displaying, the means for sensing, the means for heating, means for the powering and the means for circulating; and
a means for housing that houses the means for displaying, the means for containing, the means for receiving, the means for sensing, the means for processing, the means for powering, and the means for circulating, wherein the means for housing is configured so that the tester is portable.

14. The tester of claim 13 further comprising a means for storing a cleaning tray.

15. The tester of claim 13, wherein the means for sensing and the means for receiving are located within the means for containing.

16. The tester of claim 13, wherein the means for heating heats the diesel fuel to the gas state so that the means for sensing can sense the $SO_2$ content in the gas and determine a sulfur amount in the diesel fuel.

17. The tester of claim 13, wherein the means for sensing can detect the $SO_2$ levels from about 5 p.p.m. to about 50 p.p.m.

18. The tester of claim 13 further comprising means of indicating that the sulfur level is high or low in relation to a predetermined sulfur level.

19. The tester of claim 13, wherein the information can be directions to test the sample of diesel fuel and the amount of sulfur in the sample.

20. The tester of claim 13, wherein the means for power is a battery.

* * * * *